United States Patent [19]

Simmons et al.

[11] 4,450,110
[45] May 22, 1984

[54] AZIDO NITRAMINE

[75] Inventors: Ronald L. Simmons, Destin; Herbert L. Young, Shalimar, both of Fla.

[73] Assignee: Hercules Incorporated, Wilmington, Del.

[21] Appl. No.: 478,437

[22] Filed: Mar. 24, 1983

[51] Int. Cl.$^3$ ............................................. C07C 117/00
[52] U.S. Cl. ...................................... 260/349; 149/92
[58] Field of Search ........................... 149/92; 260/349

[56] References Cited

U.S. PATENT DOCUMENTS

| | | | |
|---|---|---|---|
| 3,697,341 | 10/1972 | Rosher et al. | 149/92 |
| 3,873,579 | 3/1975 | Rosher | 260/349 |
| 3,883,374 | 5/1975 | Rosher | 149/92 |
| 4,085,123 | 4/1978 | Flanagan et al. | 149/19.8 |
| 4,141,910 | 2/1979 | Flanagan et al. | 149/88 |
| 4,234,363 | 11/1980 | Flanagan | 149/19.4 |

*Primary Examiner*—Edward A. Miller
*Attorney, Agent, or Firm*—Edmund C. Ross, Jr.

[57] ABSTRACT

The azido nitramine 1,5-diazido-3-nitraza pentane and a method of making it are disclosed. The azido nitramine lowers flame temperature in gun and rocket propellants without visual lessening of burning rates. In addition, the azido nitramine produces low molecular weight combustion products.

1 Claim, No Drawings

AZIDO NITRAMINE

The United States Government has rights in this invention under Contract FO-8635-80C-0149, awarded by the Air Force.

BACKGROUND OF THE INVENTION

1. Field of Use

This invention relates to the azido nitramine, 1,5-diazido-3-nitraza pentane, and its preparation and use as an energetic plasticizer for solid gun and rocket motor propellants.

2. Prior Art

Azido nitramines are known. See, for example, U.S. Pat. Nos. 3,697,341; 3,883,314; 4,085,123 and 4,141,910.

The 1,5-diazido-2-nitraza pentane (or DIANP for short) of this invention produces low molecular weight combustion gases. In addition, the DIANP lowers flame temperature in propellants without lessening their burning rates. This latter feature is particularly notable. Previous experience with energetic compounds which lower flame temperatures has been that they also always lower burning rates.

3. Objects of the Invention

It is an object of this invention to provide the azido nitramine, 1,5-diazido-3-nitraza pentane, and a method for making it.

It is an object of this invention to provide plasticizer compositions for rocket and gun propellants which incorporate the 1,5-diazido-3-nitraza pentane.

These and other objects are accomplished in accordance with this invention as will be seen from the following disclosure.

BRIEF SUMMARY OF THE INVENTION

This invention relates to the azido nitramine, 1,5-diazido-3-nitraza pentane. This azido nitramine has been made by reacting diethanolamine and nitric acid to form 1,5-dinitrato-3-nitraza pentane (DINA) of the formula:

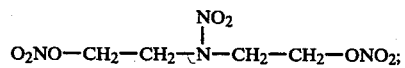

and then reacting the DINA with metal azide to form the 1,5-diazido-3-nitraza pentane (DIANP).

The DIANP is liquid at ordinary temperatures; it can serve as an energetic plasticizer for solid gun and rocket motor propellants.

DETAILED DESCRIPTION OF THE INVENTION

The 1,5-diazido-3-nitraza pentane of this invention is characterized as follows:

| Structure | $N_3-CH_2-CH_2-\underset{\underset{NO_2}{\vert}}{N}-CH_2-CH_2-N_3$ |
|---|---|
| Empirical Formula | $C_4H_8O_2N_8$ |
| Molecular Weight | 200.161 |
| Physical State | Colorless liquid |
| Density | 1.33 grams/cm$^3$ |
| Freezing Point | Supercools to below $-20°$ C. |
| Solubility | Acetone, methanol, dimethylformamide, dimethylsulfoxide (DMSO), ethyl acetate, benzene and 12.6% N nitrocellulose. Limited solubility in ethanol, isopropanol and butanol. |
| Heat of Combustion | Observed = 3899 cal/gram<br>Theoretical = 4069 cal/gram |
| Heat of Formation | Observed = 129.0 kcal/mole<br>Theoretical = 163.3 kcal/mole |
| DSC Decomposition | Exothermic decomposition @ 246° C. |
| Oxygen Balance | $-79.93\%$ |
| Nitrogen Content | 55.98% |
| Gas Molecular Weight | 16.68 |
| (based on formula $C_4H_8O_2N_8$) | |

The DIANP can be prepared by reacting diethanol amine and nitric acid. This reaction is carried out in the presence of acetc anhydride and acetyl chloride. The resulting 1,5 dinitrato-3-nitraza pentane is purified and reacted with a metal azide such as sodium azide to form the DIANP. The solvent for this latter reaction is preferably an aprotic, high boiling solvent such as dimethylsulfoxide.

The DIANP can be formulated into gun and rocket motor propellants as an energetic plasticizer. The DIANP, being liquid, is advantageously formulated with nitrocellulose as a replacement for nitroglycerin or other such explosive nitrate ester plasticizer.

The DIANP provides high burning rates at low flame temperatures. When DIANP is combined with nitrocellulose, the combination has a higher burning rate and lower flame temperature than each of the following combinations: nitrocellulose and cyclotrimethylenetrinitramine; nitrocellulose and 1,5-dinitrato-3-nitraza pentane; nitrocellulose and methylnitratoethylnitramine.

The use of DIANP also can lead to high energy outputs when used with solid and liquid energetic compounds as well as providing low gas molecular weights and flame temperatures.

Among the many propellant ingredients which can be advantageously used with the DIANP are such other solid and liquid propellant ingredients and oxidizers as glycidyl azide polymers of molecular weights between 500–10,000 (see U.S. Pat. No. 4,268,450), tetramethylenetetranitramine, triaminoguanidine nitrate (See U.S. Pat. No. 3,950,421).

The following examples illustrate this invention.

EXAMPLE 1

This example discloses preparation of the azido nitramine, 1,5-diazido-3-nitrozamine of this invention.

(a) Preparation of 1,5-dinitrato-3-nitraza pentane or DINA for short. Concentrated nitric acid (315 grams of 98% purity) was charged to a one-liter glass reactor equipped with a jacket, stirrer, thermometer and addition funnel. The temperature was controlled by circulating a 50/50 glycol/water mixture through the reactor jacket with a refrigerated circulating bath. The reactor was flushed with nitrogen and closed to the atmosphere with a drying tube filled with Drierite.

The nitric acid was cooled to 2° C. and 159 grams of diethanolamine (DEA) were added slowly beneath the surface of the acid with vigorous stirring. The top of the addition funnel extended below the surface of the acid. Time of addition was 4.2 hours, and the reaction temperature ranged from 4° C. to 8° C.; most of the addition was made at 7° C. to 8° C.

The reaction mixture was stirred at 11°–16° C. for an additional hour, and the temperature allowed to rise to 25° C. for another 30 minutes with stirring. A white precipitate formed and then dissolved at 25° C. After standing overnight, the amine/nitric acid mixture was a clear pale-yellow solution (volume=325 cc) which was transferred to an addition funnel for the second step of the reaction.

The second step was to react the amine/nitric acid mixture with acetic anhydride in the presence of a chloride catalyst to form DINA. A solution of acetyl chloride (3.34 grams) in acetic anhydride (AC$_2$O)(536 grams) was charged to the one-liter reactor, and the temperature adjusted to 31° C. The amine/nitric acid solution was added dropwise over a period of 2.3 hours with vigorous stirring.

The reaction temperature varied from 32° C. to 40° C., mostly in the range of 37° C. to 39° C. The clear pale-yellow reaction mixture was stirred at 35°–37° C. for another 1.7 hours and poured onto 3600 grams of distilled water/ice to precipitate small white crystals of crude DINA. The total volume at this point was about 4.5 liters.

The white solid DINA was filtered and washed with three 350 cc portions of distilled water. The solid DINA was partially air dried, then dissolved in 1200 cc acetone. The resulting clear pale-yellow solution was neutralized with 50 cc of 0.5-molar aqueous potassium carbonate. The acetone solution initially turned orange-red, then slowly to yellow with a pH of 8. The neutralized solution was filtered and added dropwise to 3200 grams of distilled water/ice over 1.6 hours with vigorous stirring. White flocculent crystals of DINA formed immediately and continued to form throughout the addition. After stirring for another 1.5 hours, the mixture was refrigerated overnight at 0°–5° C.

The DINA crystals were filtered and washed with four 400 cc portions of distilled water. The final two washes had a pH of 6. The yield (277 grams or 76% yield) was stored water wet. The melting point on a Fisher-Johns apparatus was 51°–51.5° C. The infrared spectrum was recorded as a Nujol mull with no discernible nitrate ester absorption at 1745 cm$^{-1}$.

According to the original synthesis developed by G. F. White and co-workers at Toronto University, the following values are typical for a 7.8-mole run of DINA:

| HNO$_3$ + | DEA + | Ac$_2$O = | DINA |
|---|---|---|---|
| 1796 gms | 907 grms | 3121 gms | 1865 gms (90% yield) |
| 28.5 moles | 8.6 moles | 30.6 moles | 7.8 moles |
| | | HNO$_3$/DEA ratio = 1.98 | |
| | | Ac$_2$O/DEA ratio = 3.44 | |

The above laboratory synthesis on a 1.5-mole scale has virtually the same weight ratios of ingredients as those specified.

(b) Preparation of 1,5-diazido-3-nitraza pentane (DIANP) The following preparation of DIANP (1,5-diazido-3-nitrazapentane) consists of essentially two steps; making a mixture of sodium azide in dimethylsulfoxide (DMSO), then reacting that with a solution of DINA in DMSO. The scale used was 0.5-mole and was conducted in a one-liter reactor.

DMSO (300 cc) was charged to a jacketed glass reactor equipped with a stirrer, thermometer, condenser and addition funnel. The temperature was controlled by circulating a 50/50 glycol/water mixture through the jacket. The reactor was flushed with nitrogen and closed to the atmosphere with a drying tube.

Sodium azide (81 grams) was charged to the reactor in small portions with vigorous stirring. Since sodium azide is only partially soluble in DMSO, some agglomeration occurred, but was readily broken up with stirring. The bulk of the sodium azide was a fine suspension.

Preheated (81° C.) glycol/water was circulated through the reactor jacket for 20 minutes. A solution of DINA (121 grams) in 200 cc DMSO was prepared under a stream of nitrogen to minimize moisture absorption during the strong cooling that occurred as DINA dissolved. The mixture was also warmed in a water bath during the dissolution. Total volume was about 290 cc. The solution was filtered to remove a small amount of fine white particulate matter.

The resulting solution of DINA in DMSO was added drop-wise to the sodium azide/DMSO mixture with vigorous stirring. The time of addition was 2.9 hours and the temperature gradually rose to 85° C. When the addition was complete, stirring was continued for 2 more hours and the temperature increased to 80° C. The reaction was then cooled to room temperature and stirring continued another 2 hours.

The reaction mixture turned a dark orange-red color when the addition of DINA/DMSO was finished, but it was clear with no observable precipitate.

To separate and purify the DIANP, distilled water (2 liters) was added to the reaction mixture at room temperature for over an hour. Stirring was continued for another 20 minutes, and a second liquid phase (orange-colored and partially emulsified) formed in the bottom of the reactor. The aqueous layer on top was dark orange-red and hazy. Total volume at this point was 2800 cc.

The aqueous layer was extracted with 600 cc portions of methylene chloride. The lower phase was dissolved in the first washing of methylene chloride. As expected, the methylene chloride extracts were colored from orange-red to yellow as the extractions continued. Small amounts of emulsion formed at the interface in all extractions, and were retained in the aqueous layer. The combined methylene chloride extracts were orange-yellow with a total volume of 1800 cc. The final aqueous phase (orange colored) was discarded.

The combined methylene chloride extracts were washed with three 600 cc portions of distilled water. During this washing, the methylene chloride extract became lighter in color, while the water washes turned yellow. After washing was complete, the methylene chloride phase (light yellow) was dried over 4A Molecular Sieves; total volume was about 1700 cc.

To purify the DIANP, the methylene chloride solution was filtered and passed through a column of neutral activated alumina, pre-wetted with methylene chloride, followed by four washes of 50 cc each of methylene chloride. An orange-colored band (1–2 mm thick) remained on top of the alumina column. The eluent of DIANP in methylene chloride was clear and colorless with a total volume of 1800 cc.

The methylene chloride was evaporated at 30°–40° C. under reduced pressure and the resulting DIANP residue was clear, very light yellow in color. The product weight was 86.7 grams or 0.433 moles for an 86% yield. The infrared spectrum was identical to DIANP purified by column chromatography.

EXAMPLE 2

A gun propellant of the formulation set forth in Table A was made on a small scale using DIANP prepared as in Example 1. The propellant was extruded into propellant granules for closed bomb testing.

TABLE A

| | |
|---|---|
| Nitrocellulose (12.6% N) | 12.50 Wt % |
| Ethyl Cellulose | 12.00 |
| 2-nitrodiphenylamine | 0.50 |
| Cyclotrimethylenetrinitramine | 50.00 |
| DIANP | 25.00 |
| Total = | 100.00 Wt % |

Closed bomb firings using the granules showed that the propellant delivered approximately 90% of theoretical energy, i.e., or delivered 349,000 ft-lb/lb impetus compared to a theoretical value of 387,000 ft-lb/lb.

EXAMPLE 3

Set forth below in Table B are results of measuring the burning rates of compositions containing DIANP (prepared as in Example 1) and nitrocellulose.

TABLE B

| COMPOSITION | Rate @ 40,000 psi (inches/sec) | $T_v$ (°K.) | Hex (cal/g) |
|---|---|---|---|
| $NC^1$ + 1% stabilizer | 4.97 | 3053[8] | 950[8] |
| NC + stab[2] + 40% DIANP[3] | 11.74 | 2854 | 830 |
| NC + stab + 40% NG[4] | 10–11 | 3850[8] | 1250[8] |
| NC + 40% DINA[5] | 8.18 | 3334 | 1083 |
| NC + 20% DINA + 20% DINAP | 9.59 | 3108 | 957 |
| NC + 40% MeNENA[6] | 7.33 | 3079 | 993 |
| NC + 20% MeNENA + 20% DIANP | 9.23 | 2971 | 912 |
| NC + 40% RDX[7] | 7.12 | 3436 | 1093 |
| NC + 20% RDX + 20% DIANP | 9.80 | 3162 | 962 |

[1]nitrocellulose (12.6% nitrogen)
[2]1% by weight of NC, 2-nitrodiphenylamine
[3]1,5-diazido-3-nitaza pentane
[4]nitroglycerin
[5]1,5-dinitrato-3-nitaza pentane
[6]methylnitratoethylnitramine
[7]cyclotrimethylenetrinitramine
[8]literature values As can be seen from the first three compositions, DIANP is burning as fast as nitroglycerin without attendant high flame temperature and heat of explosion. This phenomenon is also seen when the DIANP is mixed with other nitramines and energetic compounds, as can be seen from the next four compositions.

The last two compositions differ from the first seven in that they contain solids. As seen from the results of the last two compositions, DIANP still gives burning rate enhancement with solids (RDX) present.

EXAMPLE 4

Several energy/performance calculations were made assuming DIANP in combinations with other ingredients typically used in gun propellants. The nitrocellulose and nitroglycerin combination is presented in Table C for reference as the maximum performance in double-base propellants without resorting to energetic solids loading. As can be seen from these combinations of DIANP and energetic ingredients in Table C, DIANP can permit substantial reductions in both gas molecular weight and flame temperature with simultaneous gains in energy (defined as "Impetus" for gun propellants).

TABLE C

| COMBINATION | GAS MW[7] | $T_v$ (°K.)[7] | IMPETUS (ft-lb/lb)[7] |
|---|---|---|---|
| 40/60 $NC^1$/$NG^2$ | 27.2 | 3774 | 386,800 |
| 50/50 $RDX^3$/NC | 24.7 | 3621 | 408,200 |
| 50/50 $MeNENA^4$/NC | 22.5 | 3162 | 390,800 |
| 50/50 $TAGN^5$/RDX | 21.2 | 3330 | 437,300 |
| 40/60 NC/TAGN | 20.6 | 2771 | 373,400 |
| 50/50 DIANP/RDX | 19.9 | 3442 | 480,800 |
| 60/40 DIANP/NC | 19.5 | 2853 | 407,200 |
| 50/50 DIANP/MeNENA | 18.5 | 2983 | 448,000 |
| 30/70 DIANP/$EtNENA^6$ | 17.8 | 2523 | 393,800 |
| 50/50 DIANP/TAGN | 17.7 | 2665 | 418,900 |

[1]nitrocellulose
[2]nitroglycerin
[3]cyclotrimethylenetrinitramine
[4]methylnitratoethylnitramine
[5]triaminoguanidine nitrate
[6]ethylnitratoethylnitramine
[7]calculated using minimization of free energy.

We claim:
1. The azidonitramine composition 1,5-diazido-3-nitraza pentane.

* * * * *

Notice of Adverse Decision in Interference

In Interference No. 101,602, involving Patent No. 4,450,110, R. L. Simmons, H. L. Young, AZIDO NITRAMINE, final judgment adverse to the patentees was rendered Oct. 31, 1989, as to claim 1.
( *Official Gazette May 8, 1990* )